United States Patent [19]

Gundelfinger

[11] 3,961,534

[45] June 8, 1976

[54] TWO POSITION ROTARY VALVE FOR INJECTING SAMPLE LIQUIDS INTO AN ANALYSIS SYSTEM

[76] Inventor: Richard Gundelfinger, 6273 Chabot Road, Oakland, Calif. 94618

[22] Filed: Sept. 2, 1975

[21] Appl. No.: 609,394

[52] U.S. Cl. ......................................... 73/422 GC
[51] Int. Cl.² ........................................... G01N 1/10
[58] Field of Search....... 73/422 GC, 425.6, 425.4 P, 73/61.1 C; 210/198 C

[56] References Cited
UNITED STATES PATENTS

| | | | |
|---|---|---|---|
| 3,346,486 | 10/1967 | Winter et al. ................... | 73/422 GC |
| 3,827,303 | 8/1974 | Shiina............................ | 73/422 GC |

*Primary Examiner*—S. Clement Swisher
*Attorney, Agent, or Firm*—Lindenberg, Freilich, Wasserman, Rosen & Fernandez

[57] ABSTRACT

A two-position rotary valve for injecting a liquid sample into a stream of solvent flowing through a liquid chromatographic column, without interrupting solvent flow is disclosed. The valve is switchable between a load position and an inject position. Associated with the valve is a sample loop whose downstream end is connected to a needle cavity axially extending along the valve rotor. In the load position the upstream end of the sample loop is vented to the atmosphere. This facilitates the loading of the sample into the sample loop through the needle cavity at atmospheric pressure with a conventional syringe needle. After sample loading the syringe needle is replaced by a wire-like plug which together with a compressible seal are capable of withstanding high pressure in the needle cavity when the latter is switched to the inject position. In this position solvent flows through the sample loop and the needle cavity from the solvent source to the column, forcing the previously loaded sample onto the column.

8 Claims, 6 Drawing Figures

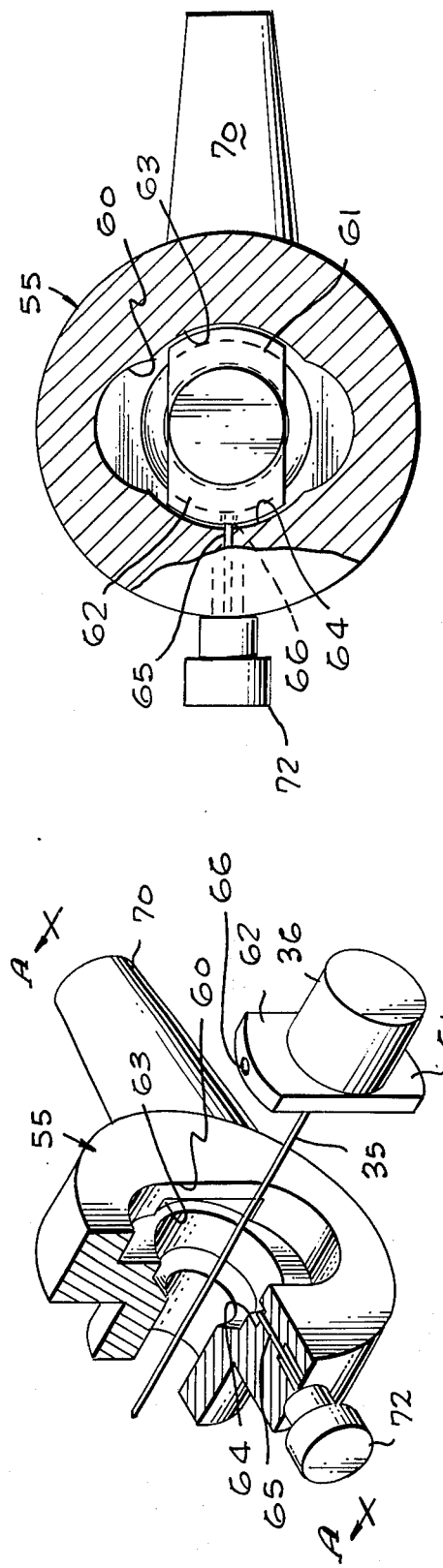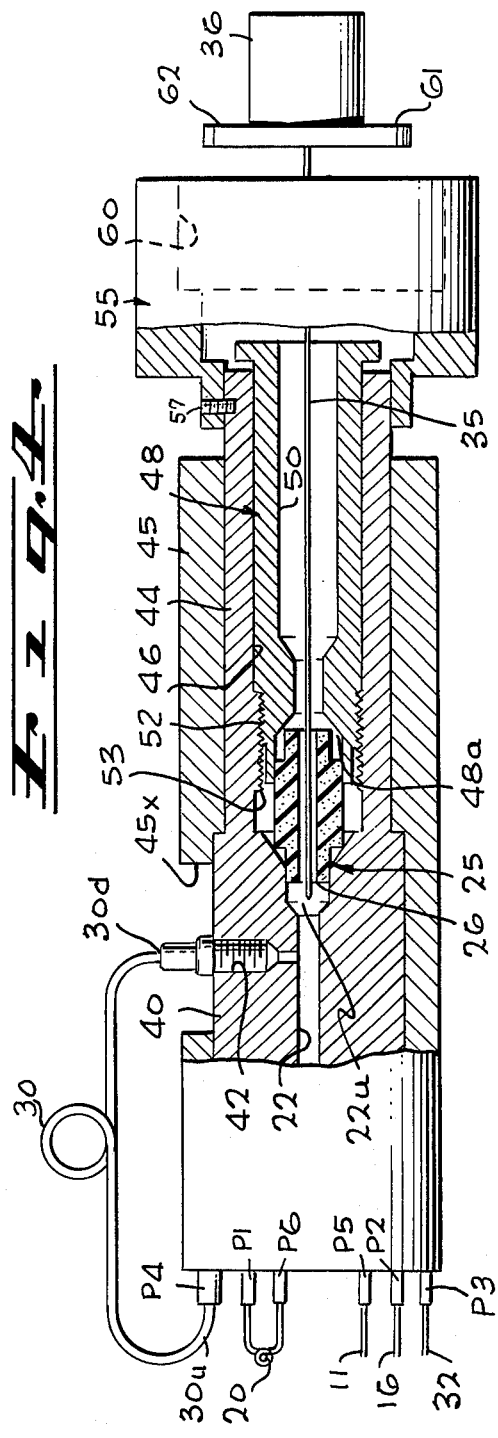

TWO POSITION ROTARY VALVE FOR INJECTING SAMPLE LIQUIDS INTO AN ANALYSIS SYSTEM

BACKGROUND OF THE INVENTION

1. Field of the Invention

The present invention generally relates to a valve for injecting a sample into a flowing stream and, more particularly, to a two-position rotary valve for injecting a liquid sample into a high pressure stream of liquid by means of a conventional low pressure volumetric syringe without loss of sample.

2. Description of the Prior Art

In the field of liquid chromatography, the contents of a liquid sample, which consists of unkown quantities of compounds, is analyzed by injecting the sample in a stream of a suitable eluting solvent, which passes through the chromatographic column and therefrom to an appropriate detector. Typically, the solvent from an appropriate source is pumped to the column by a pump, e.g., a constant flow pump. Modern columns generate relatively high back pressures under normal operation, e.g., 2000 psi and above.

For many years the fixed loop sample injection valve has been used in high pressure liquid chromatography because of its convenience of use, reliability and precision. Its major disadvantages are that a considerable amount of sample is wasted in the process of loading to insure that the sample loop is completely filled. Also, sample size can be changed only by changing the loop size. Syringe injection methods have been employed to circumvent these problems. The use of an elastomeric septum to permit direct sample injection by means of a syringe has the disadvantages of incompatibility with many eluting solvents, limitation of operating pressures to approximately 1000 psi and the requirement of special syringes with high pressure capability. Septumless injection devices have been designed for use with syringes. However, these devices require stopping the solvent flow, which is undesirable, since it usually leads to problems in stabilizing the detector signal.

Thus, a need exists for a simple, yet highly reliable sample injecting device which eliminates the disadvantages of each of the above described methods, while maintaining the advantages of reliable high pressure capability, convenient use of conventional syringes, variability of sample size, minimal sample waste, solvent compatibility and uninterrupted solvent flow.

SUMMARY OF THE INVENTION

The present invention comprises a two-position rotary valve with which a restrictor loop and a sample loop are associated. The restrictor loop is connected to the valve so that irrespective of the valve position the restrictor loop provides an uninterrupted path for solvent to flow from an appropriate solvent source to the liquid chromatographic column. The downstream end of the sample loop is connected to a needle cavity which extends axially in the valve rotor. The upstream end of the sample loop is connected to one of the external threaded fitting ports of the valve stator. In one valve position, defined as the load position, the sample loop upstream end is connected through the valve rotor to a vented port of the stator, which is at atmospheric pressure. Thus, in this position, the sample loop and needle cavity are at atmospheric pressure. In this position, the sample is loaded into the needle cavity and therefrom into the downstream end of the sample loop from a syringe needle, which extends into the needle cavity through a needle seal. After sample loading, the needle is withdrawn and a wire-shaped plug of diameter equal to that of the syringe needle is inserted through the seal into the needle cavity. The seal with the plug is capable of withstanding high pressure.

After the plug insertion the valve is switched to its second position, defined as the inject position. In this position the upstream end of the sample loop is separated from the stator vented port and is in turn connected to the stator port through which solvent is supplied to the valve. The downstream end of the needle cavity is in communication with the stator port which is connected to the column. Thus, in the inject position solvent flows in parallel in the restrictor loop and in the serially connected sample loop and needle cavity from the solvent source to the column. The sample, previously loaded into the downstream end of the sample loop, is injected onto the column with minimal delay by the solvent flowing in the sample loop and the needle cavity to the column.

The novel features of the invention are set forth with particularity in the appended claims. The invention will best be understood from the following description when read in conjunction with the accompanying drawings.

BRIEF DESCRIPTION OF THE DRAWINGS

FIG. 4 is a simplified combination block and schematic diagram of one embodiment of the two-position rotary valve;

FIG. 5 is an isometric view of a valve knob, partially broken away, and a plug holder, useful in explaining certain aspects of the invention; and FIG. 6 is a cross-sectional view of the knob along lines A—A in FIG. 5, with the plug holder in a locked position.

DESCRIPTION OF THE PREFERRED EMBODIMENTS

Figure 1:
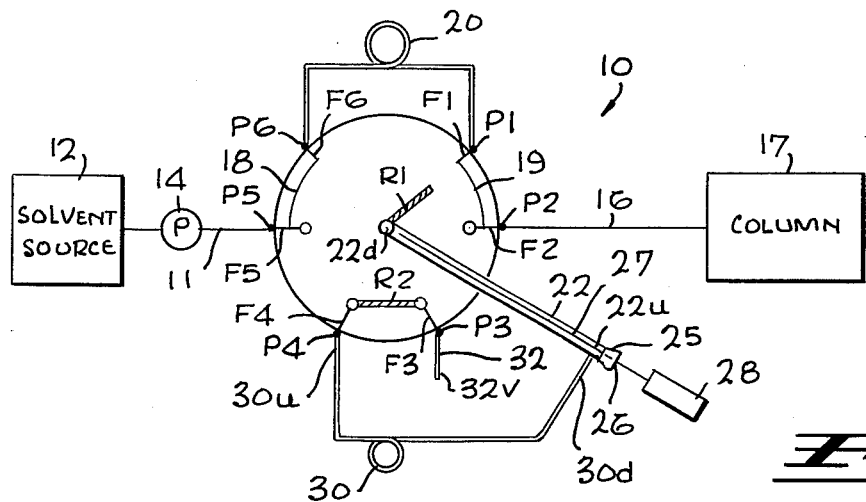
FIGS. 1 and 2 are essentially simplified combination schematic and block diagrams of the valve in the load position.

Attention is directed to FIG. 1 which is a modified schematic diagram of the novel two-position rotary switching valve 10, shown in the load position. The valve's stator includes six external threaded fitting ports, designated P1–P6 for external tubing connections. These external ports are respectively in communication with internal flow passages F1–F6 in the stator. In the particular example, port P5 is connected to a tubing 11 through which solvent from a solvent source 12 is pumped by a pump 14 to the valve. Coupled to external port P2 is a tubing 16 through which solvent with or without sample flows from the valve 10 to a liquid chromatographic column 17.

The stator has zero dead volume internal slots 18 and 19. Slot 18 interconnects flow passages F5 and F6, thereby providing a flow path from external port P5 to port P6, while slot 19 interconnects flow passages F1 and F2, thereby providing a flow path between external ports P1 and P2. Externally connected between ports P6 and P1 is a coiled length of a capillary tubing 20, hereinafter referred to as the restrictor loop 20, which is chosen to provide a selected resistance to flow therethrough. Since port P6 is connected to port P5 and port P1 is connected to port P2, a permanent path for the flow of eluting solvent, which enters the valve through port P5 and exits it through port P2 is provided between the source 12 and the column 17. This flow is uninterrupted and is independent of valve position. In the load position all of the eluting solvent flows to the column 17 through the restrictor loop 20.

The novel valve 10 includes a rotor which defines an axial needle cavity 22. The downstream end of cavity 22 designated 22d is in communication with one end of a flow passage R1 in the rotor. The other end of passage R1 in the load position is not in communication with any of the flow passages in the stator. Thus, in this position end 22d of the needle cavity 22 can be thought of as being closed off. The other end of the needle cavity 22, hereinafter referred to as the upstream end 22u, is closed or sealed off by an adjustable flexible seal 25 which defines an opening 26 through which either a needle 27 of a syringe 28 or a wire-shaped plug is insertable as will be described hereinafter in detail.

Associated with the valve 10 is a second external coiled tubing, defining a sample loop 30, whose upstream end 30u is connected to external port P4 and whose downstream end 30d is connected to needle cavity 22 near its end 22u at which the seal 25 is located. A vent tubing 32 is connected at one end to port P3 while its other end 32v is open to the atmosphere. The rotor defines a second flow passage R2. In the load position, as shown in FIG. 1, it provides a flow path between ports P3 and P4. Thus, the sample loop 30 and the needle cavity 22 are at atmospheric pressure. This facilitates the use of a conventional syringe, rather than a high pressure syringe, to load a liquid sample into the sample loop 30.

Figure 2:
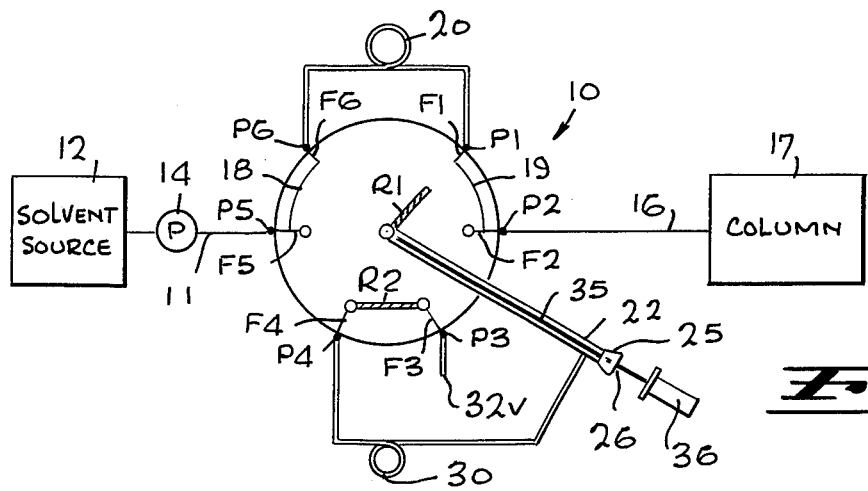

In practice, in the load position the syringe needle 27 is inserted into the cavity 22 through the opening 26 in seal 25. The desired volume of sample, preferably read off the syringe markings, is loaded into the cavity 22 through the needle 27. The diameter of the needle cavity 22 is chosen with respect to needle diameter, so that with cavity end 22d deemed as closed off, pratically all of the sample passes out of the needle tip and is loaded into the sample loop 30 through its downstream end 30d. After sample loading the syringe needle is withdrawn through seal opening 26 and a wire-shaped plug 35 of a diameter equal to that of the needle 27 is inserted into the cavity 22. FIG. 2 is the same as FIG. 1 showing the valve 10 in the load position, except that the plug 35 is shown in cavity 22 instead of the needle 27. The plug end, external to seal 26, terminates in a plug holder 36 which is lockable, as will be explained hereinafter, so that when pressure is built up in the needle cavity the plug 35 is prevented from being ejected out of the cavity through the seal opening 26. The seal 25 with the plug 35 therein is capable of withstanding relatively high pressures, e.g., 7000 psi.

Figure 3:
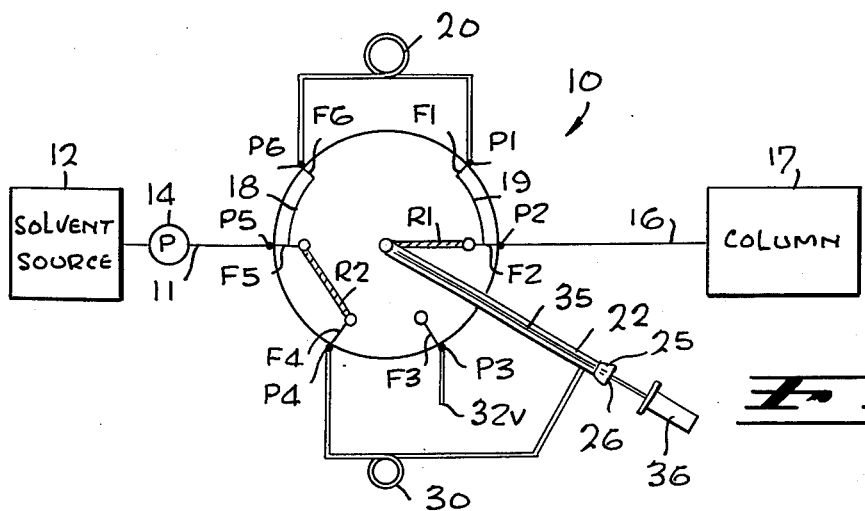
FIG. 3 is essentially a simplified combination schematic and block diagram of the valve in the inject position.

After the plug holder 36 is locked the valve is switched to its second position, defined as the inject position by rotating the rotor with respect to the stationary stator. FIG. 3 shows the valve in the inject position. In this position flow passage R1 in the rotor connects the downstream end 22d of needle cavity 22 through the stator internal flow passage F2 to port P2, to which the downstream tubing 16 is connected. Also in the inject position the flow passage R2 in the rotor connects port P4 to port P5. Thus, the upstream end 30u of the sample loop is connected to the upstream tubing 11, through which solvent is supplied to the valve. Consequently, solvent flows between upstream port P5 to downstream port P2 and therefrom to the column through the sample loop 30 and the needle cavity 22, forcing the previously loaded sample ahead of it. Since the sample was loaded into the sample loop through the downstream end 30d thereof it flows onto the column 19 with minimal delay.

It should be stressed that while in the inject position solvent flows through the sample loop and the needle cavity 22, forcing sample onto the column, the flow of solvent through the restrictor loop 20 continues uninterrupted. Thus, in the inject position solvent flows in parallel in both the restrictor loop 20 and in the sample loop 30. The lengths and internal diameters (ID) of the two loops are chosen so that a desired solvent ratio flows in the two loops in the valve's inject position.

In one embodiment actually reduced to practice, the restrictor loop ID is about 0.012 inch and that of the sample loop is 0.020. In this embodiment seven-eighths of the solvent flows through the sample loop 30 while one-eighth flows through the restrictor loop 20. It should be stressed however that in the load position (FIGS. 1 and 2) all of the solvent flows only through the restrictor loop 20. The ID of the needle cavity 22 is made sufficiently large to accommodate syringe needles of different outside diameters. In the particular embodiment which was reduced to practice the ID of the needle cavity 22 is about 0.033 to accommodate needles of 0.018 inch to 0.028 inch outside diameter (OD).

Preferably the opening 26 of the seal should have an ID compatible with the outside diameter (OD) of the syringe needle used to load the sample and the plug which is used to replace the needle prior to switching the valve to the inject position. However, as will be described hereinafter the seal 25 is compressible so that if desired the ID of opening 26 may be chosen to accommodate the largest needle to be used. The seal may be compressed to reduce the ID opening 26 so as to accommodate therein needles and plugs of smaller OD, yet be able to withstand the high pressure when solvent flows through the sample loop and the needle cavity.

Attention is now directed to FIG. 4 which is a simplified combination side and cross-sectional view of one embodiment of the valve of the present invention. It is shown with the plug 35 partially inserted therein. In FIG. 4 numeral 40 designates the rotor with its axially aligned needle cavity 22. A threaded fitting port 42 extends from the cavity 22 to the rotor periphery. It is the downstream end 30d of the sample loop 30, which is connected to port 42. The rotor 40 from which a rotor shaft 44 extends are housed in the stator housing 45. The latter defines a slot 45X to provide access for the sample loop downstream end 30d to port 42.

The rotor shaft 44 has an axial opening 46 designed to accommodate a bushing 48 with an axial opening 50. A recess 48a in bushing 48 accommodates one end of seal 25. Threads 52 on the outer surface of bushing 48 are provided. These mesh with threads 53 in the inner surface of shaft 44. Thus, the bushing 48 is threadable in and out of the shaft 44. The seal 25 with its opening 26 aligned with cavity 22 and bushing opening 50 is supported at one end by the bushing 48 while its other end is accommodated in the upstream end 22u of cavity 22 in rotor 40.

The seal 25, which is flexible, is compressible as the bushing 48 is threaded into the shaft 44. When compressed the ID of the opening decreases so that when the plug 35 passes therethrough the seal, it is tightly pressed against the plug as well as at the upstream end 22u of the cavity 22 to prevent any solvent leakage therebetween, when solvent at high pressure flows through the cavity in the inject position of the valve.

In practice the plug 35 has an OD equal to that of the syringe needle to be used. The bushing 48 is threaded into the shaft 44 to compress the seal sufficiently to form a relatively tight fit between the plug 35 and the seal 25. Thus, the tightness of the seal 25 is such that it effectively seals both the plug 35 and the syringe needle without further adjustment. In operation, with the valve in the load position, the plug 35 is withdrawn and the syringe needle 27 is inserted into the cavity 22 to load the sample (see FIG. 1). Thereafter the needle is withdrawn and replaced by the plug 35. The plug holder 36 is lockable in a valve knob 55 which is fastened to the rotor shaft by set screws 57.

One embodiment of the knob which was actually reduced to practice and the manner in which the plug holder is lockable therein may best be described in connection with FIGS. 5 and 6. FIG. 5 is an isometric view of the knob 55 partially broken away and the plug 35 with its plug holder 36. FIG. 6 is a cross sectional view along lines A—A in FIG. 5 showing the plug holder in the locked position. The knob has an oval-shaped opening 60, whose center is axially aligned with opening 50 of bushing 48. One of the functions of opening 60 is to enable the plug holder 36, from which flanges 61 and 62 extend and which form part of the plug holder 36, to be inserted into the knob 55. The knob has a pair of recesses 63 and 64 which extend inwardly from opening 60 in a direction perpendicular to its major axis.

In operation to lock the plug holder 36 to the knob 55 the former is inserted through opening 60 and thereafter is rotated 90° so that flanges 61 and 62 are in recesses 63 and 64, respectively. The front end of a spring loaded pin 65 extends into recess 64 so that when the flange 62 is accommodated in recess 64 the front end of the pin 65 is engaged in a recess 66 in flange 62, thereby further securing the plug holder in the locked position.

As shown in these figures a handle 70 extends from knob 55 to facilitate the turning of the knob to switch the valve from one position to the other. Opposite handle 70 a pullable knob 72 is located. When pulled it retracts the pin 65 from recesses 64 and 66 thereby enabling the plug holder 36 to be rotated 90° and withdrawn from the knob through oval shaped opening 60.

From the foregoing it should be appreciated that with the two-position rotary valve of the present invention a sample can be loaded into a stream of solvent flow and thereafter inject the sample onto a liquid chromatographic column without interrupting the solvent flow. The sample is loaded into the sample loop when the valve is in the load position, in which the pressure in the sample loop is at atmospheric pressure. Consequently, a conventional rather than a high pressure syringe can be used for sample loading. When the valve is switched to the inject position (FIG. 3) solvent flows through the sample loop and forces the previously loaded sample ahead of it for injection onto the column. The sample loop 30, which is external to the valve, is chosen to be able to contain the largest volume of sample expected to be loaded, without any of the sample spilling over and being vented through vent 32v. However, it should be pointed out that the sample loop need not be filled with the sample which is injected into it through its downstream end. Any volume desired, up to the maximum capacity of the sample loop can be introduced by the conventional syringe. None of the sample is wasted and all of it gets injected onto the column.

To withstand high pressure, e.g., on the order of 7000 psi, the seal 25 is provided. Through its opening 26 a needle of a conventional syringe is inserted to load the sample. Then the needle is replaced by a wire-like plug, which together with the seal 25, effectively seal the upstream end of the needle cavity and withstand the high pressure in the latter without leaking, when the valve is switched to its inject position. Both the syringe needle and the plug are easily insertable into the needle cavity through the seal which is accessible through an opening in the valve knob and an aligned opening in a bushing. The latter is threadable to the rotor shaft to appropriately compress the seal so as to enable it to withstand the high pressure when the valve is in the inject position. It should thus be apparent that with the two-position rotary valve of the present invention, a sample can be injected with a conventional syringe for subsequent high pressure injection of the sample onto a column, without any loss of sample.

Although particular embodiments of the invention have been described and illustrated herein, it is recognized that modifications and variations may readily occur to those skilled in the art and consequently, it is intended that the claims be interpreted to cover such modifications and equivalents.

The embodiments of the invention in which an exclusive property or privilege is claimed are defined as follows:

1. For use in combination with a source of liquid from which liquid flows at a selected pressure greater than atmospheric pressure to a liquid receiver, a rotary valve, positionable in either a first position, definable as a load position, or a second position, definable as in inject position, for injecting a liquid sample into the liquid stream from said source to said receiver, the valve comprising:

a stator including a plurality of external ports and a corresponding plurality of internal liquid flow paths in communication with said ports, said ports including first and second ports connectable to said source and receiver, respectively, a third port vented to atmospheric pressure, and a fourth port;

an external conduit defining a fixed length sample loop having an upstream end connected to said fourth port and a downstream end;

rotable rotor means defining a needle cavity connected to the sample loop downstream end, and defining an upstream end and a downstream end, said rotor means further defining first and second rotor flow passages, said first rotor passage providing a flow path between the cavity downstream end to the stator internal path in communication with said second port only when said valve is in said inject position, and said second rotor passage providing a flow path between the stator internal paths in communication with said third and fourth ports when said valve is in said load position, and between the stator internal paths in communication with said first and fourth ports when said valve is in said inject position, said rotor means further including seal means for sealing the cavity upstream end, said seal means defining an opening accessible from the valve exterior for facilitating the insertion of a syringe needle into said cavity therethrough for injecting a liquid sample into said sample loop through said cavity; and plug means for effectively closing the opening of said seal means, said seal means with said plug means being adapted to withstand said selected pressure when liquid flows through said cavity at said selected pressure when said valve is in said inject position, said plug means comprising an elongated wire having a front portion thereof insertable into said cavity through the seal means opening to thereby close the latter, and a lockable plug holder connected to the wire end opposite the front portion which is insertable into said cavity.

2. The combination as described in claim 1 wherein said valve includes means connected to said rotor means for locking the plug holder thereto to retain the wire front portion in said cavity when said valve is in said inject position and the liquid flowing in said cavity is at said selected pressure.

3. The combination as described in claim 1 wherein the downstream end of said sample loop is connected to said cavity near the cavity upstream end adjacent said seal means.

4. The combination as described in claim 3 wherein said needle cavity is an elongated cavity having an inner diameter only sufficiently large to accommodate the syringe needle therein, with substantially all of the sample injected into the cavity through said needle passing in the cavity around said needle to said sample loop.

5. For use in combination with a source of liquid from which liquid flows at a selected pressure greater than atmospheric pressure to a liquid receiver, a rotary valve, positionable in either a first position, definable as a load position, or a second position, definable as an inject position, for injecting a liquid sample into the liquid stream from said source to said receiver, the valve comprising:

a stator including a plurality of external ports and a corresponding plurality of internal liquid flow paths in communication with said ports, said ports including first and second ports connectable to said source and receiver, respectively, a third port vented to atmospheric pressure, and a fourth port;

an external conduit defining a fixed length sample loop having an upstream end connected to said fourth port and a downstream end;

rotatable rotor means defining a needle cavity connected to the sample loop downstream end, and defining an upstream end and a downstream end, said rotor means further defining first and second rotor flow passages, said first rotor passage providing a flow path between the cavity downstream end to the stator internal path in communication with said second port only when said valve is in said inject position, and said second rotor passage providing a flow path between the stator internal paths in communication with said third and fourth ports when said valve is in said load position, and between the stator internal paths in communication with said first and fourth ports when said valve is in said inject position, said rotor means further including seal means for sealing the cavity upstream end, said seal means defining an opening accessible from the valve exterior for facilitating the insertion of a syringe needle into said cavity therethrough for injecting a liquid sample into said sample loop through said cavity; and plug means for effectively closing the opening of said seal means, said seal means with said plug means being adapted to withstand said selected pressure when liquid flows through said cavity at said selected pressure when said valve is in said inject position, said rotor means being rotatable about a selected axis, with said needle cavity being an elongated cavity axially aligned with said selected axis.

6. The combination as described in claim 5 wherein said plug means comprises an elongated wire having a front portion thereof insertable into said cavity through the seal means opening to thereby close the latter, and a lockable plug holder connected to the wire end opposite the front portion which is insertable into said cavity.

7. The combination as described in claim 6 wherein said valve includes means connected to said rotor means for locking the plug holder thereto to retain the wire front portion in said cavity when said valve is in said inject position and the liquid flowing in said cavity is at said selected pressure.

8. The combination as described in claim 7 wherein the downstream end of said sample loop is connected to said cavity near the cavity upstream end adjacent said seal means, said needle cavity is an elongated cavity having an inner diameter only sufficiently large to accommodate the syringe needle therein, with substantially all of the sample injected into the cavity through said needle passing in the cavity around said needle to said sample loop.

* * * * *